United States Patent
Ro

[11] Patent Number: 5,888,208
[45] Date of Patent: Mar. 30, 1999

[54] MODULAR HIP TRIAL FOR LONG STEMS

[75] Inventor: Gloria Ro, North Quincy, Mass.

[73] Assignee: Johnson & Johnson Professional, Inc., Raynham, Mass.

[21] Appl. No.: 884,588

[22] Filed: Jun. 27, 1997

Related U.S. Application Data

[63] Continuation-in-part of Ser. No. 824,336, Mar. 26, 1997.

[51] Int. Cl.$^6$ ..................................................... A61F 2/36
[52] U.S. Cl. .................................. 623/23; 606/63; 606/86
[58] Field of Search ................................ 606/86, 89, 90, 606/92, 99, 100, 102, 63; 623/18–21, 22, 23

[56] References Cited

U.S. PATENT DOCUMENTS

| | | | |
|---|---|---|---|
| 4,135,517 | 1/1979 | Reale | 128/303 |
| 4,163,292 | 8/1979 | Averett, Jr. | 623/23 |
| 4,404,691 | 9/1983 | Buning et al. | 623/23 |
| 4,601,289 | 7/1986 | Chiarizzio et al. | 128/305 |
| 4,908,032 | 3/1990 | Keller | 623/23 |
| 4,919,678 | 4/1990 | Krantz | 623/23 |
| 4,938,773 | 7/1990 | Strand | 623/23 |
| 5,032,130 | 7/1991 | Schelhas et al. | 623/23 |
| 5,074,879 | 12/1991 | Pappas et al. | 623/18 |
| 5,080,685 | 1/1992 | Bolesky et al. | 623/23 |
| 5,100,407 | 3/1992 | Conrad et al. | 606/79 |
| 5,108,437 | 4/1992 | Kenna | 623/16 |
| 5,108,452 | 4/1992 | Fallin | 623/23 |
| 5,342,366 | 8/1994 | Whiteside et al. | 606/102 |
| 5,507,817 | 4/1996 | Craig et al. | 623/18 |
| 5,507,830 | 4/1996 | DeMane et al. | 623/23 |
| 5,531,785 | 7/1996 | Love et al. | 606/99 |
| 5,569,263 | 10/1996 | Hein | 606/102 |
| 5,601,567 | 2/1997 | Swajger et al. | 606/102 |
| 5,653,765 | 8/1997 | McTighe et al. | 623/23 |
| 5,683,472 | 11/1997 | O'Neil et al. | 623/22 |

OTHER PUBLICATIONS

Brochure entitled Perfecta PDA Calcar, dated Oct. 1995.
Howmedica hnr brochure, including article entitled *Head/Neck Replacement Surgery in Hip Fractures of the Elderly*, by Ronald Joseph, M.D., Ph.D., Orthopaedic Surgeon, Good Samaritan Hospital, San Jose, California, pp. 2–15, ©Jul. 1993.
Howmedica hnr brochure, *Head/Neck Replacement*, 4 pages dated Jul. 1993.
Zimmer Modular Calcar brochure, 5 pages showing tools and Steps 1–16, ©1992.
Wright Medical Technology, Inc. brochure entitled *Perfecta/PDA*, 4 pages, ©1996.
Brochure entitled *Cemented Hip Systems Surgical Technique*, Johnson & Johnson Orthopaedics, pp. 1–8, dated May 1996.

*Primary Examiner*—Michael J. Milano
*Assistant Examiner*—Tram A. Nguyen
*Attorney, Agent, or Firm*—Nutter, McClennen & Fish, LLP

[57] ABSTRACT

A calcar trial includes a stem having a proximal end and a distal end, and a body. The body is engaged with the stem near the proximal end of the stem and is slidable with respect to the stem. A locking mechanism inhibits movement of the body with respect to the stem when desired. A collar extends radially outward from the stem to surround a portion of the body. The body and stem are configured so that the diameter of the calcar trial at a point between the collar and the distal end of the stem increases as the body is moved toward the distal end of the stem and decreases as the body is moved away from the distal end of the stem. The proximal end of the stem can include opposed notches that are egagable by a forked tool. A curved distal stem portion can be secured to the distal end of the stem.

11 Claims, 5 Drawing Sheets

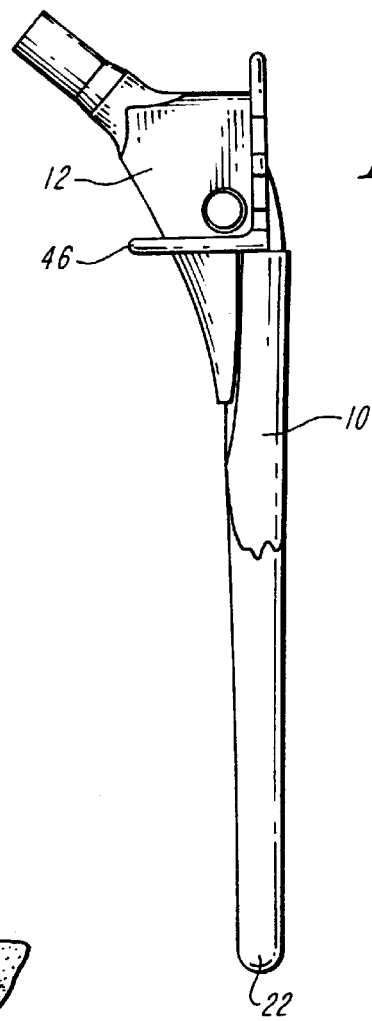
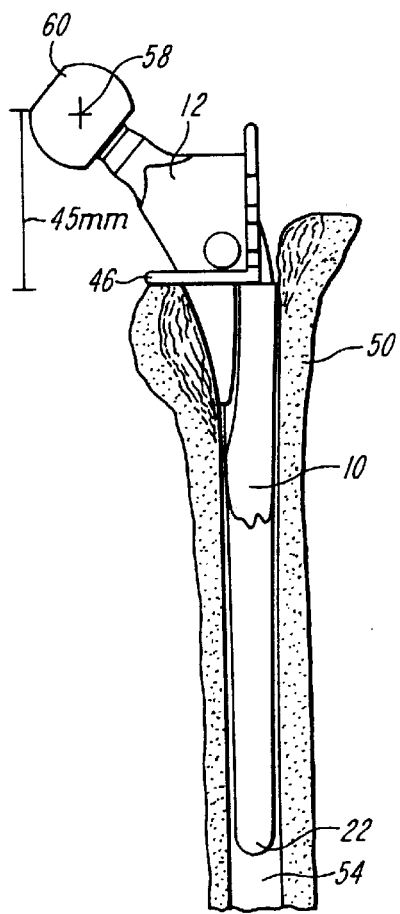
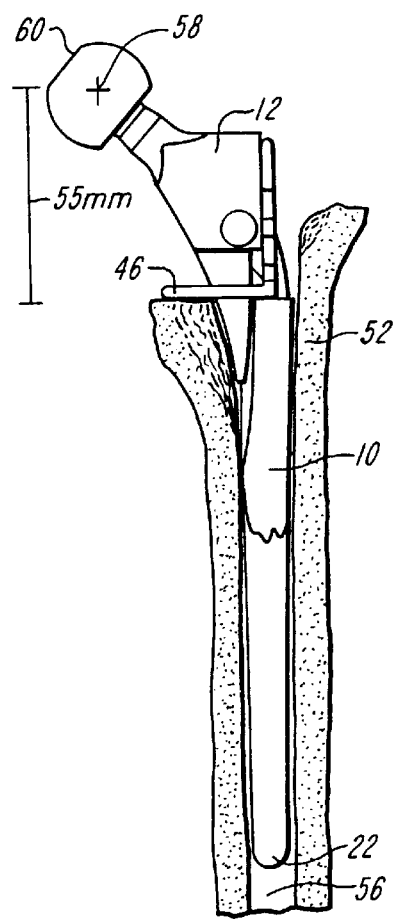

MODULAR HIP TRIAL FOR LONG STEMS

CROSS REFERENCE TO RELATED APPLICATIONS

This application is a continuation-in-part of U.S. Ser. No. 08/824,336, filed Mar. 26, 1997.

STATEMENT REGARDING FEDERALLY-SPONSORED RESEARCH

Not Applicable.

FIELD OF THE INVENTION

The present invention relates to a device used in hip arthroplasty, such as a trial for determining the required dimensions of a prosthetic femoral component, and more particularly to a trial for a calcar stem.

BACKGROUND OF THE INVENTION

A successful hip replacement or arthroplasty procedure results, in part, from selection of prosthetic joint components that are dimensioned and positioned to closely approximate or replicate the geometry and functional characteristics of a natural, healthy hip joint. Typically, the component selection process includes a pre-operative analysis of joint images. However, it has been discovered that a valuable adjunct to image analysis is the temporary fixation of one or more provisional components to a bone or bones of interest at a stage of the arthroplasty procedure prior to permanent fixation of the prosthetic joint. The provisional components are intended to mimic certain aspects of the permanent prosthetic joint in order for a surgeon to validate measurements and to test or "try-out" several different possible component sizes and configurations. Hence, provisional components are aptly known as "trials."

In a known procedure, a trial for a femoral component is used in the following manner. The proximal end of a femur is resectioned and the medullary canal of the femur is reamed. A broach is inserted into the resected proximal end of the femur to provide a cavity within the bone dimensioned and contoured to receive a femoral stem. However, prior to removing the broach, a trial neck or trunnion and trial head can be secured to the broach to simulate a complete femoral stem. Normally, several neck and head trials of varying lengths and geometries are successively joined to the broach in an attempt to determine an appropriate neck length and overall femoral stem length. Once these lengths have been determined, the trial neck and head are removed from the broach and the broach is removed from the femur. Subsequently, a femoral stem of the appropriate length is selected for insertion into the cavity defined by the broach using techniques known to those skilled in the art.

Other techniques require that the broach be removed from the medullary canal to allow a trial having a stem portion to be used, in addition to a trial head and neck. For example, U.S. Pat. No. 5,100,407 discloses a system including a group of variously sized trial neck/body portions and a group of differing length trial stem portions which are mixed and matched to create a suitable trial. However, repetitive removal and insertion of successions of trial stems accompanied by successive assembly and disassembly with respect to the body can consume a lengthy and costly period of time.

Another known trial includes a stem to which a collar is secured at successive points along the length of the trial until an appropriate neck length and stem length have been ascertained. Undesirably, this type of trial induces measurement inaccuracies resulting from stem movement as the collar is repeatedly engaged with and disengaged from the stem. Additionally, as the collar is moved toward the distal end of the stem, less and less of the stem is disposed within the medullary canal, causing the trial to become increasingly unstable and rendering accurate measurements very difficult to achieve.

In addition to other deficiencies of known trials, it is believed that a trial system consisting of numerous parts that must be selected and mated in various combinations, possibly many times, is cumbersome, unnecessarily complex and a waste of valuable time.

SUMMARY OF THE INVENTION

The present invention overcomes the disadvantages of known trials by providing a unified assembly that facilitates very accurate measurements in a convenient, easy to use manner. The trial does not require repeated assembly and disassembly, and it is uniquely able to provide a geometry that closely approximates a broached cavity, regardless of the height of the trial.

In an exemplary embodiment, a calcar trial includes a stem having a proximal end and a distal end, and a body. The body is engaged with the stem near the proximal end of the stem and is slidable with respect to the stem. A locking mechanism can be provided for inhibiting movement of the body with respect to the stem. A collar can extend radially outward from the stem to surround a portion of the body. The body and stem can be configured so that the diameter of the calcar trial at a point between the collar and the distal end of the stem increases as the body is moved toward the distal end of the stem and decreases as the body is moved away from the distal end of the stem. Additionally, the proximal end of the stem can include engagement structures such as opposed notches that are engagable by a forked tool.

In another embodiment of the invention, a calcar trial includes a proximal stem portion engagable with a distal stem portion. A single distal stem portion can be curved and reversibly securable to the proximal stem portion to provide a long stem trial suitable for procedures for either the right or the left femur. The trial can include a slidable body portion to allow the height of the trial to be adjusted.

BRIEF DESCRIPTION OF THE DRAWINGS

A more complete understanding of the present invention and the attendant advantages and features thereof will be more readily understood by reference to the following detailed description when it is considered in conjunction with the accompanying drawings, wherein:

FIG. 6 is a side view of the trial of FIG. 1 in an assembled configuration;

FIG. 7 is a side view of the trial in accordance with the invention inserted into a femur at a first body height;

FIG. 8 illustrates a trial in accordance with the invention inserted into a femur at a second body height;

DETAILED DESCRIPTION OF THE INVENTION

Figure 1:
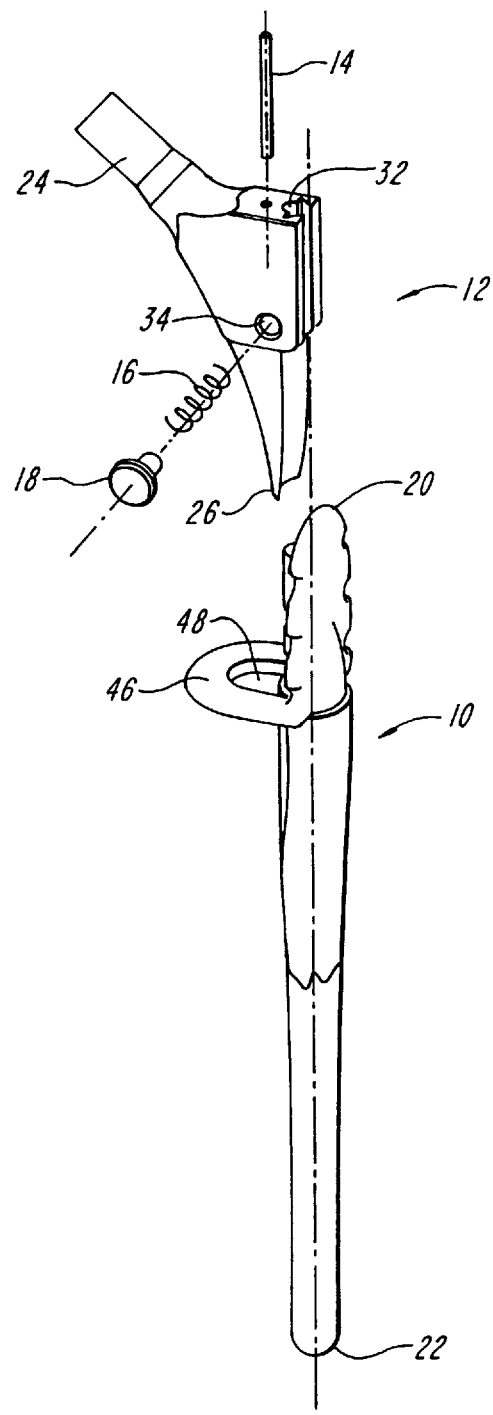
FIG. 1 is an exploded view of the trial in accordance with the invention that illustrates a body portion and a stem portion.

Referring to FIG. 1, a trial in accordance with the invention is shown in an exploded view to show a stem 10, a body 12, a pin 14, a spring 16, and a push-button 18. The stem 10 has a proximal end 20 and a distal end 22, and the body 12 has a proximal end defining a trunnion 24 and a distal end 26. The body 12 is engagable with the stem 10 near the proximal end of the stem so as to be slidable with respect to the stem a predetermined distance between the proximal end and the distal end of the stem.

Figure 2:
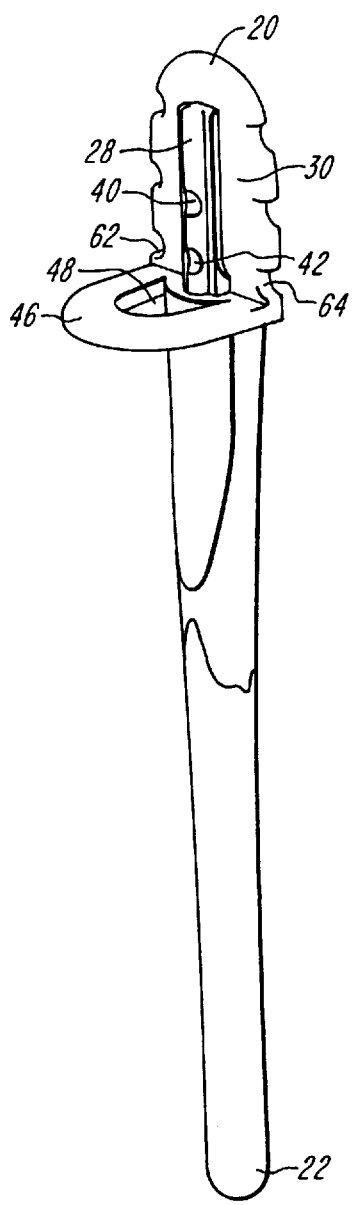
FIG. 2 is a perspective view of the stem portion of the trial shown in FIG. 1.

A guide or track can be associated with either or both of the body 12 and the stem 10 to guide movement of body with respect to the stem. For example, as shown in FIG. 2, the stem 10 includes a track 28 protruding from a first face or vertical flange 30 of the stem and extending a predetermined distance between the proximal end 20 and the distal end 22 of the stem. As shown in FIG. 1, the body 12 includes a notch 32 for receiving the track 28. However, in other embodiments, the body 12 includes a raised portion that is engagable with a track that is recessed within the stem. Regardless of its configuration, the complimentary guide/track/notch of the body and stem serve to limit movement of the body 12 along a predetermined path, such as longitudinal movement, as well as to inhibit undesired movements such as twisting or lateral displacement.

Figure 4:
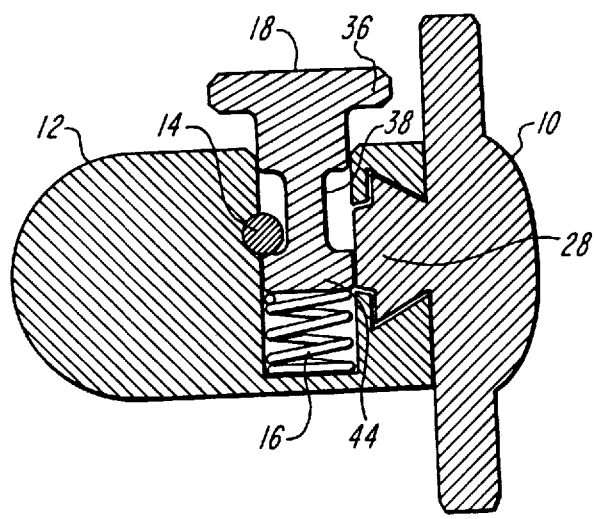
FIG. 4 is a sectional view of a trial showing a locking mechanism in an engaged position.
Figure 5:
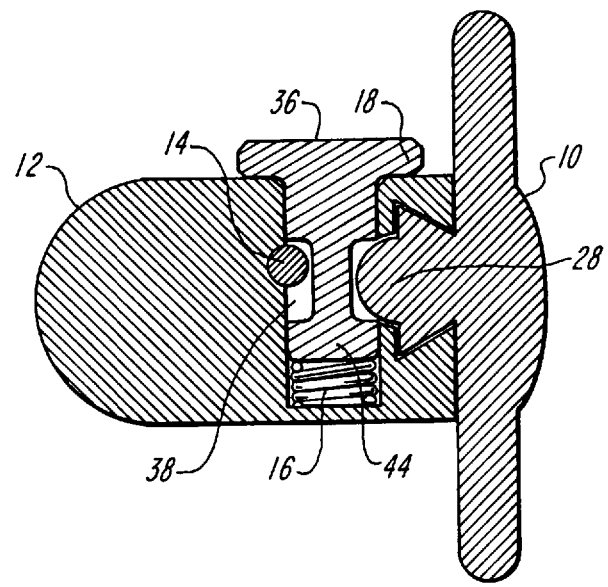
FIG. 5 is a sectional view of a trial showing the locking mechanism in a disengaged position.
Figure 3:
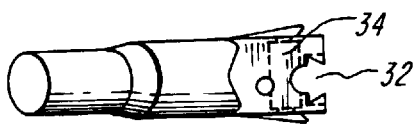
FIG. 3 is a top view of the body portion illustrated in FIG. 1.

Additionally, a locking mechanism can be provided for inhibiting movement of the body 12 with respect to the stem 10. As shown in FIGS. 1 and 3, the body 12 can include a channel 34 that is transverse to the notch 32 and which is adapted to receive an elongate portion of the button 18 therein. The button 18 is movable within the channel from a first position, wherein a portion of the button contacts and engages a portion of the track 28 of the stem, to a second position wherein the button is disengaged from the track. As shown in FIG. 4, the button 18 is biased to the first position by the spring 16. FIG. 5 illustrates the button 18 in the second position. The button 18 includes an expanded head portion 36 that engages the body 12 to limit insertion depth of the button 18 into the body. The button 18 also includes a cut-out portion 38 into which the pin 14 and a portion of the track 28 are received. It will be noted most clearly in FIG. 2 that the track includes first and second transverse grooves 40 and 42. When the body 12 and the stem 10 are caused to slide with respect to each other, the cut-out portion 38 rides over/along the track 28 until a groove 40, 42 is reached, whereupon an end portion 44 of the button is biased into the groove 40, 42. The end portion 44 is released from the groove 40, 42 by pushing the button 18 into the body 12 with enough force to overcome the bias force of the spring 16.

Referring again to FIGS. 1 and 2, a collar 46 extends radially outward from the stem. The collar 46 surrounds a portion of the body 12, as shown in FIG. 6, and it is dimensioned to be disposed on a resectioned bone surface as shown in FIGS. 7 and 8. The collar 46 and the distal end of the stem 22 are a fixed distance apart. The collar defines an aperture 48 having curves to compliment the shape of the body 12 and into which the body is received.

Turning now to FIGS. 7 and 8, use of the calcar trial is illustrated with respect to resectioned femurs 50 and 52 respectively. Once the femur has been prepared to receive the trial, the distal end 22 of the trial is inserted into the medullary canal 54, 56. It should be noted that in both FIGS. 7 and 8 the full length of the stem 10 from the collar 46 to the distal end of the stem 22 is inserted into the medullary canal. This enables a surgeon to verify that the medullary canal has been reamed to a sufficient depth and width to accommodate a replacement hip stem. The surgeon then slides the body 12 with respect to the stem as required to adjust the head height or distance between a reference point 58 on a head 60 affixed to the body 12 and the collar 46 to determine a prosthetic hip stem length. In FIG. 7, the body 12 is positioned with respect to the stem 10 at a head height of 45 mm, whereas in FIG. 8 the head height is 55 mm. The trial is then removed from the medullary canal and a prosthetic hip stem having the determined length is selected from a group of hip stems. The selected hip stem is cemented into the medullary canal.

It should be noted in these illustrations that the proximal portion of the trial underneath the collar is wider than an intermediate portion of the stem or its distal end 22 to ensure a tight fit of the trial within the femur. The trial is slightly larger than an actual replacement stem in the proximal section below the collar to. allow the trial to fill the medullary canal which has been reamed to be slightly larger than an actual replacement stem (to leave room for bone cement to surround the replacement stem). Also, the stem 10 and the body 12 are configured so that a diameter of the trial at a point between the collar and the distal end of the stem increases as the body is moved toward the distal end of the stem and decreases as the body is moved away from the distal end of the stem. Thus, regardless of where a resection cut is made, the dimensions and shape of the trial correspond to the dimensions and shape of the broached medullary canal.

Figure 9:
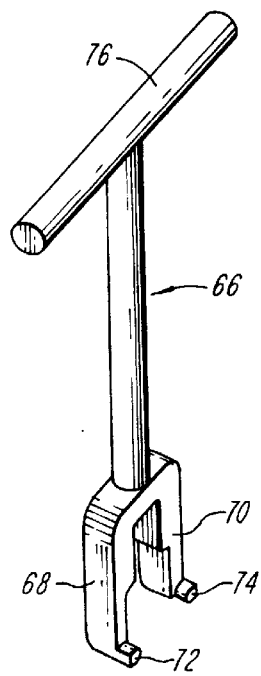
FIG. 9 is a perspective view of an inserter/extractor tool.

As the trial is usually seated within the medullary canal very snugly, the trial in accordance with the invention further includes features that are of use when inserting the trial into or extracting the trial from the medullary canal. For example, referring to FIG. 2, the proximal end of the stem includes a tool engagement structure, such as a pair of opposed notches 62 and 64 on the stem. A tool 66, shown in FIG. 9, includes a first fork portion or furcation 68 and a second furcation 70 for engaging the opposed notches 62 and 64. The space between the furcations corresponds to the shape of the body 12 to allow the tool to snugly interfit with the body. This ensures that the tool remains axially aligned with the body 12 and the stem 10. Each furcation 68 and 70 can include angled end portions or tines 72 and 74, respectively. A handle 76 provides an easily graspable structure for pulling or pushing tool 66 as well as a suitable surface for mallet striking. Because the notches 62, 64 are similar to the notches of a replacement stem, used to orient cerclage cables, the same tool 66 can be used to insert and extract both the trial and the replacement stem.

Figure 10:
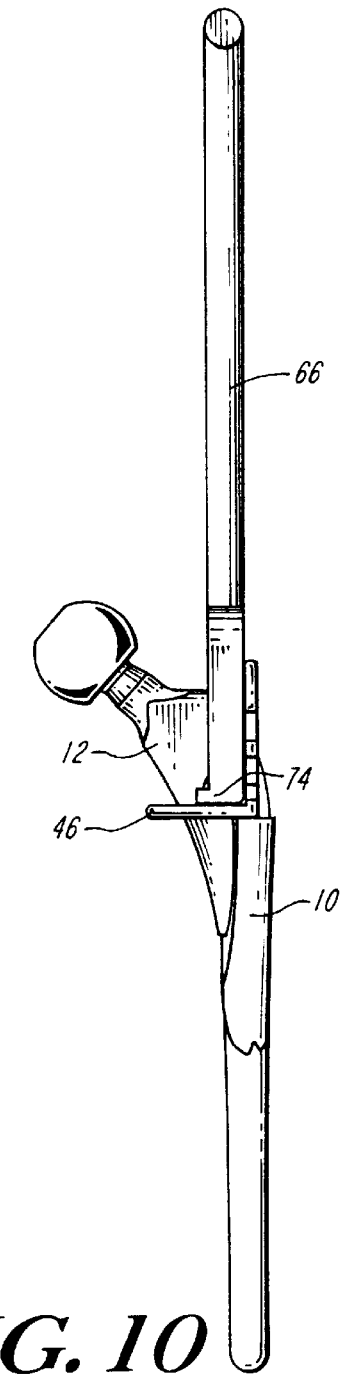
FIG. 10 illustrates the tool of FIG. 9 engaged with a trial for insertion of the trial into a femur.

FIG. 10 shows the tool 66 positioned with respect to the trial for insertion of the trial into a medullary canal, wherein the tines 72, 74 are not engaged with the notches 62, 64, but rest directly upon the collar 46 on opposite sides of the body 12.

Figure 11:
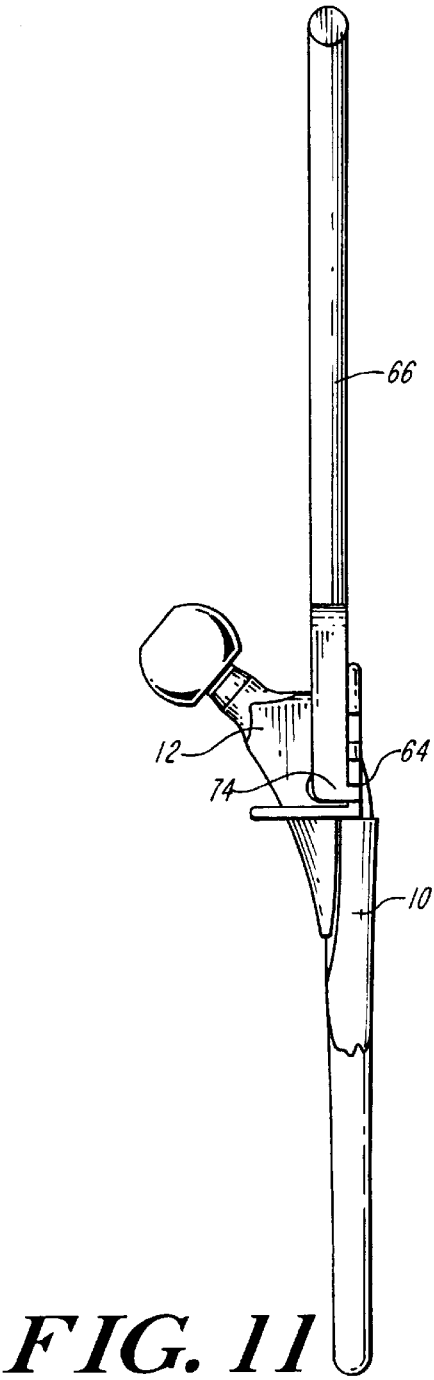
FIG. 11 illustrates the insertion/extraction tool in an extraction position.

FIG. 11 shows the tool 66 positioned with respect to the trial for extraction of the trial from a medullary canal, wherein the tines 72, 74 are engaged with the notches 62, 64. The forked tool thus allows an even and distributed force to be applied to the stem 10 during both insertion and extraction.

Yet another problem with trials, particularly trials for long hip stems, is that a long trial must account for the curvature or bow of the femur. Accordingly, the present invention further provides a modular stem that, depending on the configuration of a distal stem portion, can lengthen the trial stem and provide required curvature for appropriate femoral implantation.

Figure 12:
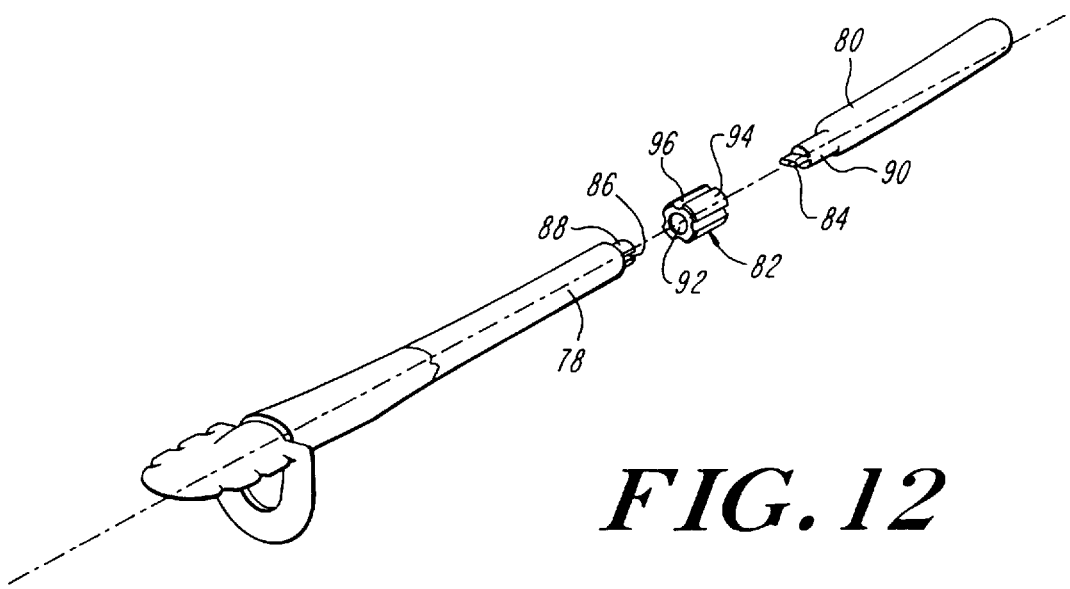
FIG. 12 is an exploded view of an embodiment of a trial having a modular stem portion.

For example, FIG. 12 is an exploded view of an embodiment of a trial having a proximal stem portion 78, a distal stem portion 80, and a connecting element 82. The proximal stem portion 78 can include one or more of the features described above with respect to engagement of a body 12 or with respect to a tool 66. Alternatively, the proximal stem portion 78 can include none of the above inventive features, but rather features found in trials known in the art.

In the illustrated embodiment, the proximal stem portion 78 is about the same length as the stem portion 10 illustrated in FIGS. 1–11 and is therefore usable as described above without the addition of the connecting element 82 or the distal stem portion 82. However, when the distal stem portion 80 is joined to the proximal stem portion 78 the total length of the trial is equivalent to that of a traditional single-piece, long-stem trial. In other embodiments, the proximal stem portion 78 is longer or shorter than the stem portion 10, and the distal stem portion 80 is correspondingly shorter or longer than that illustrated in FIG. 12.

Although the distal stem portion 80 can be straight or coaxial with the proximal stem portion 78, in the illustrated embodiment it is curved or includes an angulation so that some or all of the distal stem portion is not coaxial with the proximal stem portion. The curvature or the angulation can be provided by the shape of the distal stem portion and/or by joining the stem portions together at an angle. Collectively, curvature or angulation of the stem or stems is referred to as "curved."

Continuing to refer to FIG. 12, the distal stem portion 80 is selectively, reversibly attachable to the proximal stem portion 78 to cause the trial to have a curve in a first or a second opposing direction. Thus, the trial can be used for either the right or the left femur without requiring an additional part. In the illustrated embodiment, structures that facilitate reversibility include a tang 84 on the distal stem portion 80 that is receivable within a slot 86 defined by the proximal stem portion 78. The tang 84 and the slot 86 ensure that the distal and proximal stem portions are mated at a precise orientation, and that the orientation cannot be inadvertently changed. For example, were the stem portions to be joined simply by friction fitting a cylindrical element into a cylindrical bore, or by a threaded connection, precise orientation could not be assured.

The slot 86 and tang 84 can be located on reduced diameter portions 88 and 90 of the respective proximal stem portion 78 and the distal stem portion 80. The reduced diameter portions 88 and 90 can be threaded and receivable within a threaded bore 92 of the connecting element 82. The connecting element 82 can include texturing such as alternating elongate ridges 94 and depressions 96 to enable the connecting element to be grasped by hand or with a tool and rotated with respect to the stem portion or portions to create a threaded engagement between the stem portions. Thus, the connecting element locks the stem portions together. However, other embodiments are contemplated that allow the stem portions to be joined in one of two or more precise orientations and be held together without a separate connecting element.

Figure 13:
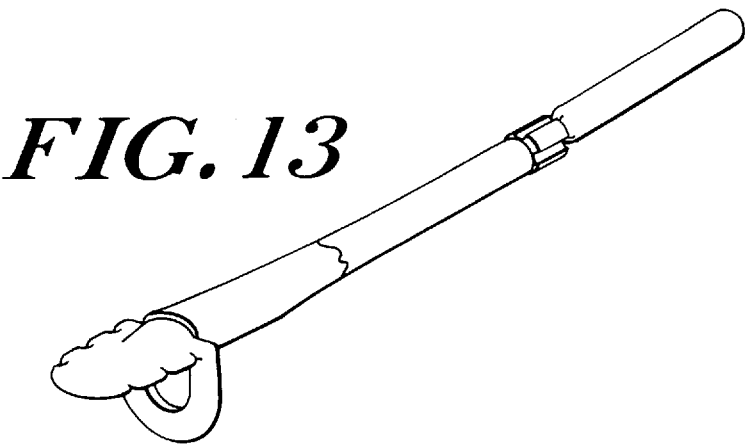
FIG. 13 depicts the trial of FIG. 12 in an assembled state.

FIG. 13 depicts the trial of FIG. 12 in an assembled state. It should be noted that the connecting element 82 has a maximum diameter that approximates that of the stem portions where they join the connecting element.

Figure 14:
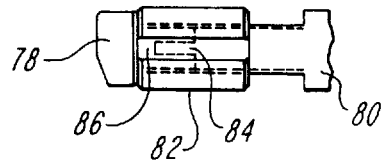
FIG. 14 is a partial cut-away view of a connection between a first stem portion and a second stem portion.

FIG. 14 is a partial cut-away view of a connection between the proximal stem portion 78 and the distal stem portion 80 which clearly shows the engagement of the tang 84 with the slot 86. Although the illustrated tang and slot provide an excellent reversible connection, other structures for joining the stem portions are contemplated and the particular connection is not a limitation of the invention.

Although the invention has been shown and described with respect to exemplary embodiments thereof, various other changes, omissions and additions in form and detail thereof may be made without departing from the spirit and scope of the invention.

What is claimed is:

1. A calcar trial comprising:
   a proximal stem portion having a proximal end and a distal end;
   a body adjustably engaged with the proximal stem portion so as to be longitudinally slidable with respect to the proximal stem portion such that the proximal stem portion is substantially externally disposed with respect to the body; and
   a curved distal stem portion having a proximal end and a distal end, the proximal end of the distal stem portion being selectively engagable with the distal end of the proximal stem portion.

2. The calcar trial of claim 1, further comprising a connecting element having a first end and a second end, the connecting element being interposable between the proximal end of the distal stem portion and the distal end of the proximal stem portion, wherein the connecting element is releasably securable at the first end to the distal end of the proximal stem portion and releasably securable at the second end to the proximal end to the distal stem portion.

3. The calcar trial of claim 1, wherein the distal stem portion includes a tang at the proximal end thereof and wherein the distal end of the proximal stem portion defines a slot for receiving the tang.

4. The calcar trial of claim 1, wherein the distal stem portion is engagable with the proximal stem portion in a first orientation to cause the distal stem portion to curve in a first direction with respect to the proximal stem portion, and wherein the distal stem portion is engagable with the proximal stem portion in a second orientation to cause the distal stem portion to curve in a second direction with respect to the proximal stem portion.

5. The calcar trial of claim 4, wherein the first direction is opposite from the second direction.

6. The calcar trial of claim 2, wherein the connecting element includes a threaded bore and wherein the distal end of the proximal stem portion and the proximal end of the distal stem portion are threaded and insertable into the bore of the connecting element.

7. The calcar trial of claim 6, wherein an outer surface portion of the connecting element is textured.

8. The calcar trial of claim 6, wherein the outer surface of the connecting element includes a plurality of ridges and depressions.

9. A calcar trial comprising:
- a proximal stem portion having a proximal end and a distal end; and
- a connecting element, having a proximal end externally mountable to the distal end of the proximal stem portion and a distal end; and
- a distal stem portion having a proximal end and a distal end, the proximal end of the distal stem portion engagable with the distal end of the connecting element in a first orientation to cause the distal stem portion to curve in a first direction with respect to the proximal stem portion, and the distal stem portion engagable with the distal end of the connecting element in a second orientation to cause the distal stem portion to curve in a second direction with respect to the proximal stem portion.

10. The calcar trial of claim 9, wherein the first direction is opposite from the second direction.

11. A hip replacement system comprising:
- a trial for a prosthetic femoral implant including a proximal stem portion having a proximal end and a distal end;
- a body slidably engaged with the proximal stem portion, wherein the body is slidable a predetermined distance between the proximal end and the distal end of the proximal stem portion;
- a vertical flange that is wider than the body and which includes a pair of opposed notches on opposites side of the body; and
- a plurality of distal stem portions, wherein the distal stem portions are securable to the distal end of the proximal stem portion.

* * * * *